United States Patent [19]

Alexander et al.

[11] Patent Number: 4,783,331

[45] Date of Patent: Nov. 8, 1988

[54] METHOD FOR SOLUBILIZATION OF ASPARTAME IN EFFERVESCENT AQUEOUS SYSTEMS; AND COMPOSITION

[75] Inventors: Thomas A. Alexander, South Bend; Lawrence J. Daher, Elkhart, both of Ind.

[73] Assignee: Miles Inc., Elkhart, Ind.

[21] Appl. No.: 66,951

[22] Filed: Jun. 29, 1987

[51] Int. Cl.⁴ .................. A61K 9/46; A61K 9/62; A61K 33/10

[52] U.S. Cl. ..................... 424/44; 424/156; 424/466

[58] Field of Search ............ 424/466, 44, 156; 514/965

[56] References Cited

U.S. PATENT DOCUMENTS

| | | | |
|---|---|---|---|
| 4,083,950 | 4/1978 | Duvall et al. | 424/44 |
| 4,650,669 | 3/1987 | Alexander et al. | 424/466 X |
| 4,680,323 | 7/1987 | Lowey | 514/965 X |
| 4,704,269 | 11/1987 | Korab | 424/466 X |

OTHER PUBLICATIONS

Ivanovich et al., "The Absorption of Calcium Carbonate", Annals of Internal Medicine, vol. 66, No. 5, pp. 917-923, (May 1967).

*Primary Examiner*—Michael Lusignan
*Attorney, Agent, or Firm*—Mary G. Boguslaski

[57] ABSTRACT

A method and composition for providing aspartame as a sweetener in effervescent calcium ion-generating systems is provided. The method includes a step for providing a selected surfactant in association with the aspartame sweetener, to provide for aqueous solution of the aspartame in the presence of the solubilized calcium without film formation and without excessive foaming. Preferably, the aspartame/surfactant is provided by a granule composition, utilized in association with a calcium carbonate/citric acid effervescent couple.

35 Claims, No Drawings

METHOD FOR SOLUBILIZATION OF ASPARTAME IN EFFERVESCENT AQUEOUS SYSTEMS; AND COMPOSITION

FIELD OF THE INVENTION

The present invention relates to effervescent calcium tablets and in particular to effervescent calcium tablets including an artificial sweetener such as aspartame therein. The invention concerns a method for preparing an aspartame-containing calcium tablet that effervesces with substantially complete formation of solution, without excessive foaming and/or film formation.

BACKGROUND OF THE INVENTION

It has long been known that calcium is a required nutriment for the human body. Frequently calcium carbonate ($CaCO_3$) is used as a dietary supplement to provide the needed calcium. In part, this is due to the fact that calcium carbonate is more easily solubilized in the gastrointestinal tract than are many other calcium salts, due to its solubility in acidic solutions.

Some individuals have trouble taking calcium carbonate in solid form. For certain of these individuals, the problem is simply a matter of physical difficulty with ingesting $CaCO_3$ tablets, which may be large or hard to chew. Others may find the taste unacceptable. Still others appear to lack sufficient acid in their gastrointestinal juices to ensure solution. Such individuals may excrete most ingested calcium carbonate, without sufficient absorption. See for instance, Ivonovich, Fellows and Rich, "The Absorption of Calcium Carbonate", *Annals of Internal Medicine,* Volume 66, No. 5, pp. 917–923 (May 1967).

If water-insoluble calcium carbonate cannot be converted to the soluble calcium chloride form in vivo, a soluble form of calcium must be administered. Also, a solution of calcium will be preferred by those individuals who have difficulty ingesting solid $CaCO_3$ tablets.

An approach developed to accomplish solubilization of calcium carbonate, in an orally administered aqueous solution, has been through the development of an effervescent system. Effervescent antacids are well-known, an example being ALKA-SELTZER PLUS disclosed in the U.S. Pat. No. 4,083,950. Such systems generally include an alkaline material, such as sodium bicarbonate, sodium carbonate, potassium bicarbonate, or potassium carbonate, in combination with an organic acid such as citric acid, fumaric acid, or adipic acid. When such a system is placed in water, the carbonate and the acid react to form carbon dioxide and a water soluble salt of the alkali metal cation An efficient effervescent system, analogous to the antacids but for the delivery of calcium carbonate, comprises calcium carbonate granules compressed into a tablet with an organic acid preferred effervescent composition of this type comprises, by weight: approximately 90–10% $CaCO_3$; 10 to 90% organic acid component; and 2 to 20% compression-enhancing vehicle. (U.S. Pat. No. 4,650,669)

The compression-enhancing vehicle assists tablet formation, while protecting the carbonate/acid couple from premature reaction. It is preferably a substance such as lactose, which can form a coating on the calcium carbonate.

The organic acid is preferably, by weight, at least 80% citric acid. A reason for this is a preference, by most individuals, for the taste of citric acid and its salts.

Flavorings such as grapefruit, lemon and orange may be added to such compositions improve taste. Also, sweeteners, lubricants, vitamins and other adjuvants may be included.

Aspartame is a desired sweetener for utilization in such solutions. It is a widely used low-calorie sugar substitute, typically prepared from L-aspartic acid and L-phenylalanine. It is available under the trade name NutraSweet ® from G. D. Searle and Co., Chicago, Ill.

In use, one or more calcium carbonate-containing effervescent tablets are dissolved in water, to be orally taken by the subject. It has been found that when aspartame is added to such tablets, the effervescent system is adversely affected. In particular, when the aspartame is present in sufficient amount to serve as an effective sweetener, filming occurs; that is, an undesirable film forms. The film tends to adhere to, and climb, the sides of a container in which the effervescence takes place. Such a film is aesthetically undesirable. Further, it may adversely affect taste and texture, and it may hinder complete solution of all constituents of the tablet.

It is desirable to utilize the low calorie sweetener aspartame in calcium carbonate-containing effervescent compositions. Therefore, there is a need for a method by which aspartame may be included in such compositions with control of film formation.

SUMMARY OF THE INVENTION

According to the invention, certain nonionic surfactants are utilized in association with aspartame, as ingredients in calcium carbonate-containing effervescent tablets. These surfactants enhance the ability of the aspartame to dissolve completely and without film formation or filming.

It has been found that a variety of surfactants will effectively eliminate film formation. However, many surfactants also lead to excessive foam formation during effervescence. Such foaming is undesirable, as it is aesthetically displeasing, and it may make the resulting calcium-containing solution more difficult to drink.

A preferred group of surfactants utilizable to achieve aspartame solution without film formation and without excessive foaming has been identified. The group comprises block copolymers of propylene oxide and ethylene oxide.

The particular surfactant composition used, the total amount of surfactant present in the effervescent composition, the weight ratio between aspartame and surfactant, and the method of formation of the effervescent compound are the factors of major concern to the formulation of the compositions according to the present invention. Upon effervescence, the present compositions yield a solution of aspartame and organic acid calcium salt, without excessive foaming and without undesirable film formation According to the present invention, a method of inhibiting film formation, during generation of an aqueous solution containing soluble calcium and aspartame, includes the provision of a nonionic surfactant comprising a block copolymer of propylene oxide and ethylene oxide in the solution. The copolymer preferably has an average molecular weight of between about 2,000 and 4,000. The poly(oxypropylene) base of such surfactants generally has an average molecular weight of between about 1,500 and 3,500 and preferably 1,700–3,000. The hydrophilic poly(oxyethylene) component comprises between about 15% and 35% and preferably 20-30% of the copolymer average molecular weight.

Preferred effervescent tablets for delivery of solubilized calcium are formed from calcium carbonate granules, organic acid particles and aspartame granules The present invention concerns the provision of aspartame granules which, when used in an effervescent tablet, yield aspartame solution without film formation and/or excessive foaming The aspartame granules contain sufficient aspartame to effectively sweeten the final solution, and sufficient nonionic surfactant to inhibit film formation and foaming. The preferred nonionic surfactants for such use are as described above.

In general, problems with film formation may be expected whenever aspartame is dissolved in calcium ion-containing solutions. As is described in detail below, both calcium and aspartame appear to contribute to the filming problem. Thus, the present invention encompasses a general method of providing for solution of aspartame and calcium ions without filming and excessive foaming.

DETAILED DESCRIPTION OF THE INVENTION

In accord with the present invention, aspartame is included in a calcium carbonate-containing effervescent tablet. The preferred tablet includes calcium carbonate-containing granules and aspartame-containing granules. The aspartame granules include a nonionic surfactant which facilitates effervescence and complete solution without film formation and without excessive foaming. The tablets also contain an organic acid which, during effervescence, reacts with the calcium carbonate to form carbon dioxide and the organic acid calcium salt.

All percentages are percent by weight, unless otherwise designated

The Calcium Carbonate Granules

The calcium carbonate granules contain $CaCO_3$ and compression-enhancing vehicle. These components preferably are as described below.

Calcium Carbonate

Calcium carbonate employed in the present invention should be in a particulate form. Calcite particles are preferred, since aragonite produces loss of clarity in the solution, upon effervescence. A suitable particulate calcium carbonate for utilization in the calcium carbonate granules is Albaglos ®, available from Pfizer (Adams, Mass.).

Compression-Enhancing Vehicle

The calcium carbonate particles are coated with a compression-enhancing vehicle. The compression-enhancing vehicle facilitates compression of the components into tablet form and prevents premature reaction of the calcium-carbonate with the organic acid.

Preferred compression-enhancing vehicles include lactose, maltose and dextrose. One such agent is MALTRIN ® M100, a malto-dextrin which is a hydrolyzed corn product (cereal solids) available from Grain Processing Corp. (Muscatine, Ia.). Another useful agent is Lactose 316 Fast-Flo, a lactose composition available from Foremost Foods.

Calcium carbonate granules for use in tablets according to the present invention generally include: calcium carbonate about 75-90%, preferably about 80-85%; lactose component, at least about 5-15%; and hydrolyzed cereal solids, about 5-10%. However, these amounts may be varied, so long as the $CaCO_3$ is sufficiently coated to prevent premature reaction.

A variety of methods may be used to coat the calcium carbonate particles with the compression-enhancing vehicle. These may include wet granulation, dry granulation, fluid bed granulation, and spray drying. Spray drying is generally preferred.

The coated calcium carbonate granules should have an average particle diameter of less than about 400 microns, and more preferably less than about 250 microns. A particularly suitable average particle diameter is about 44 microns. If the coated particle size is too large, undissolved $CaCO_3$ particles may result during effervescence. Also, tablet formation may be difficult. If the particle size is too small, handling problems may result.

The calcium carbonate granules may be prepared by dry-mixing the components and suspending the mix in water to form a 1:1 weight/weight slurry. The resultant slurry is then spray dried. Preferably the calcium carbonate granule size obtained is about 40-60% $>70$ microns and not more than about 30% $\leq 44$ microns.

The Organic Acid Component

The organic acid component of the tablet, which reacts to form the calcium salt upon effervescence, preferably includes a major amount of citric acid, and may include one or more other organic acids. It is preferred that the organic acid component be at least about 80%, e.g. about 85-100% citric acid. Preferred adjuvants are fumaric acid, adipic acid and glutamic acid. The inclusion of a high proportion of these organic acids, relative to the amount of citric acid, is not desirable due to taste considerations. The anhydrous form of citric acid, rather than the monohydrate form, is generally preferred.

The organic acid component preferably is in a particulate form, wherein the particles have a larger average diameter than the calcium carbonate granules. The distribution for the average particle size is about 10% $\geq 250$ microns and 15% $\leq 74$ microns with the preferred range being 20% $\geq 177$ microns and 3% $\leq 44$ microns.

The Aspartame-Containing Granules

As indicated above, the preferred method of tablet formation comprises mixing aspartame granules with calcium carbonate granules and organic acid particles, and tabletting the mixture. Adjuvants may be included, as well as additional amounts of the compression-enhancing vehicle.

The aspartame granules preferably contain aspartame, compression-enhancing vehicle and sufficient nonionic surfactant to inhibit film formation. The compression-enhancing vehicle may be the same as that described hereinabove for the calcium carbonate granules.

The Surfactant

Useful surfactant components for the aspartame-containing mixtures are nonionic surfactants which are block copolymers of propylene oxide and ethylene oxide. The compounds include both a hydrophobic poly(oxypropylene) unit and a hydrophilic poly(oxyethylene) unit. Such surfactants generally exhibit relatively low foaming, solubility in both water and organic solvents, low reactivity and little tendency to form gels.

Preferred surfactants of this type for use according to the present invention have an average molecular weight range of 2,000–4,000, more preferably 2,500–3,700. Surfactants found particularly useful for the present invention exhibit an average molecular weight range for the poly(oxypropylene) component of about 1,500–3,500, and preferably 1,700–3,000. The hydrophilic poly(oxyethylene) component of such compounds is about 15–35%, and preferably 20–30%, of the average polymer molecular weight.

The synthesis of such nonionic polyols is usually initiated by addition as propylene oxide to propylene glycol initiator. The resulting hydrophobe or hydrophobic base is prepared in the desired length. Then, addition of ethylene oxide sandwiches the hydrophobic poly(oxypropylene) block between hydrophilic poly(oxyethylene) units.

Three such surfactants have been identified as useful in aspartame/calcium ion solutions according to the present invention. These surfactants are: Pluronic® L-62 polyol; Pluronic®L-72 polyol and Pluronic® L-92 polyol, from BASF Wyandotte Corp. (Wyandotte, Mich.). The Cosmetic, Toiletry and Fragrance Association (CTFA)-assigned names for these compounds are as follows:

| BASF Wyandotte | CTFA Name |
|---|---|
| Pluronic ® L-62 polyol | Poloxamer 182 |
| Pluronic ® L-72 polyol | Poloxamer 212 |
| Pluronic ® L-92 polyol | Poloxamer 282 |

Table I below lists some of the properties of these surfactants.

TABLE I

| Product | Average Molecular Weight | Form | Brookfield Viscosity cps[a] | Specific Gravity a/25° C. | Cloud Point (1% aqueous sol.) °C. | Surface Tension dynes/cm 0.1%, 25° C. | Pour Point °C. | Dynamic Foam Height[6], mm | HLB Value, 25° C. | Average Molecular Weight of Poly(oxypropylene) Hydrophobe |
|---|---|---|---|---|---|---|---|---|---|---|
| Poloxamer 182* (Pluronic L-62) | 2500 | Liquid | 450 | 1.03 | 32 | 42.8 | −4 | 35 | 7.0 | 1750 |
| Poloxamer 212 (Pluronic L-72) | 2750 | Liquid | 510 | 1.03 | 25 | 39.0 | −7 | 20 | 6.5 | 2050 |
| Poloxamer 282 (Pluronic L-92) | 3650 | Liquid | 700 | 1.03 | 26 | 35.9 | 7 | 25 | 5.5 | 2750 |

[a]Measured for liquids at 25° C.
[b]0.1% solution at 400 ml/minute at 49° C.
*Low foaming grade also available from BASF Wyandotte

Preparation of the Aspartame-Containing Granule

The weight ratio of aspartame to surfactant in the aspartame-containing granule, and thus in the effervescent tablet, should be between about 2.5–350:1, and preferably is between about 18–25:1. As the examples indicate, larger amounts of surfactant appear to cause excessive foaming.

Generally, the aspartame-containing granule is prepared as follows: a dry mix of the compression-enhancing vehicle, for example lactose, and aspartame is prepared. To this mix, in a high shear granulator, an aqueous solution of surfactant is added which is effective to disperse the surfactant throughout the aspartame mix. When distribution is complete, the granular product is spread on paper and dried, preferably with heating to between about 120°–130° Fahrenheit (F.) (48°–55° C.), e.g., for about three hours.

A preferred aspartame granule can be prepared from a dry blend of the lactose ingredient (65–95%) and the aspartame (5–35%). To this blend, in a high shear granulator (Patterson-Kelly Liquids/Solids granulator with granulator intensifier bar) is added a sufficient quantity of an aqueous solution including 2–10% of the surfactant and about 90–98% de-ionized water. Sufficient surfactant solution is added to deliver the final amount of surfactant desired per weight of aspartame, typically between 1:2.5–350 and preferably between 1:18–25 as indicated above. When the mixture is homogeneous the resultant granular product is dried.

Adjuvants

The effervescent tablet may include flavorings, vitamins, lubricants and other adjuvants or supplements. For example, grapefruit, orange or lemon flavorings may be used Fumaric acid may be added as a lubricant, and sorbitol as a tabletting aid. The effervescent couple may also include such antacids such as sodium bicarbonate, sodium carbonate, potassium bicarbonate, potassium carbonate and mixtures thereof

Method of Manufacture of the Effervescent Tablets

To prepare effervescent tablets incorporating calcium carbonate, aspartame and nonionic surfactant according to the present invention, typically calcium carbonate-containing granules, aspartame-containing granules, and organic acid particles, prepared as described above, are mixed with the compression enhancing vehicle and any adjuvants, and are formed into a tablet Conventional tabletting techniques may be used.

The finished product tablet preferably contains about 10–90% calcium carbonate and about 90–10% citric acid. Preferably the amounts of calcium carbonate and organic acid are stoichiometrically proportional, so there will be complete reaction of each. If another alkaline component, such as sodium bicarbonate, is used, additional acid may be needed to complete the reaction.

Typically, the tablet should contain aspartame in a range of about 0.1–10.0% by weight of the $CaCO_3$. A preferred range is 0.5–5.0% by weight of the $CaCO_3$. For preferred tablets, the aspartame should be about 0.03–3.3%, and preferably 0.2–0.5% of the entire tablet A preferred tablet composition includes about 30–45% calcium carbonate granules, about 25–70% citric acid, about 1–5 % fumaric acid, about 0.3–5% aspartame granules and about 0.5–15% compression-enhancing vehicle in addition to the compression-enhancing vehicle used in forming the calcium carbonate-containing granules and the aspartame-containing granules. Preferred calcium carbonate granules include about 75–90% and preferably about 80–85% $CaCO_3$ and about 5–25% lactose-containing compression-enhancing vehicle. Also, the calcium carbonate granules preferably include about 5-10% hydrolyzed cereal solids. Preferred aspartame granules include about 5-35% aspartame, about 65-95% compression-enhancing vehicle and about 0.1-2.5% of the nonionic surfactant component. As indicated previously, excess surfactant should be avoided or excessive foaming may result.

A preferred tablet has a mass of about 2,600 to 5,000 mg and provides for the delivery of about 500 milligrams (mg) of calcium upon effervescence. A general formulation for suich a tablet is given in Table II, below.

TABLE II

| Ingredient | mg/Tablet |
|---|---|
| CaCO$_3$ granules[a] | about 1,200–1,800 |
| Citric Acid powder | about 1,000–2,800 |
| Sorbitol | about 50–300 |
| Lactose | about 25–100 |
| Fumaric Acid, micronized | about 100–200 |
| Flavoring | about 0.5–10 |
| Aspartame Granules[b] | about 35–150 |

[a]The CaCO$_3$ granules used in the above composition preferably contain: CaCO$_3$ 1,000–1,500 mg; Lactose (Lactose 316 Fast-Flo), 100–200 mg; and, Cereal solids, 75–125 mg.
[b]The aspartame granules used in the above composition preferably contain: Aspartame, 10–15 mg; Surfactant, 0.3–1.0 mg (poloxamer 182, poloxamer 212 or poloxamer 282); and, Lactose (Lactose 316 Fast-Flo), 25–125 mg.

The above components are mixed and formed into a one-inch diameter tablet. Conventional means may be employed.

Specific formulations for the delivery of 500 mg calcium are given in Table III, below.

TABLE III

| Ingredient | mg/Tablet |
|---|---|
| Example 1 | |
| CaCO$_3$ granules[a] | 1510.6 |
| Citric Acid powder (Miles Laboratories, Inc.) | 1825.0 |
| Sorbitol, Fine granule (E. Merck & Co.) | 90.0 |
| Fumaric Acid, micronized | 124.3 |
| Flavoring | 6.5 |
| Aspartame Granules[b] | 63.6 |
| | 3620.0 |
| Example 2 | |
| CaCO$_3$ granules[a] | 1510.6 |
| Citric Acid powder (Miles | 1825.0 |

TABLE III-continued

| Ingredient | mg/Tablet |
|---|---|
| Laboratories, Inc.) | |
| Sorbitol, Instant (E. Merck & Co.) | 239.3 |
| Lactose 316 Fast-Flo (Formost Foods) | 75.0 |
| Fumaric Acid, micronized | 130.0 |
| Flavoring | 6.5 |
| Aspartame Granules[b] | 113.6 |
| | 3900.0 |

[a]The CaCO$_3$ granules comprise: CaCO$_3$, 1253.8 mg; Lactose (Lactose 316 Fast-Flo), 151.1 mg; and, Cereal solids, 105.7 mg.
[b]The aspartame granules comprise: Aspartame (APM), 13.0 mg; nonionic Surfactant, 0.6 mg; and, Lactose (as Lactose 316 Fast-Flo), 100.0 mg.

Method of Use of the Effervescent Tablets

For a typical use, two tablets, each capable of delivering about 500 mg of calcium ion, are dissolved in about 4–5 ounces (118–150 milliliters) of cool water. Effervescence occurs to form the calcium/aspartame solution. After the reaction has been allowed to finish, the solution may be ingested.

EXAMPLES

Study of Film Formation and Foaming

Various tablet compositions were prepared employing the ingredients listed in Table III, Example 2, above, but with the modifications and variations in components as indicated. For each composition a test was conducted by placing two tablets in about 150 ml of tap water, at about 24°–27° Centigrade (C.). The water was contained within a 500 ml graduated cylinder, so that relative amounts of foam and film formation could be measured. The volume of foam is defined as the maximum volume observed during effervescence, minus the volume of the final solution (about 160 ml).

Variations in the procedure used to form the test tablets depended primarily on the surfactant being incorporated and tested. In some instances the surfactant or other modifier was not introduced into an aspartame granule but was dry blended with the other components of the tablet. In other instances, the modifier was mixed with the aspartame and citric acid by trituration.

The compositions of the test tablets, are given in the following Table IV.

TABLE IV

| Tablet Formula | Modifier (to control film formation) | Quantity (mg) | Method of Addition | % concentration in aspartame (APM) granule (where appropriate) | | % concentration in final tablet formula | |
|---|---|---|---|---|---|---|---|
| 1 | B-cyclodextrin[a] | 2.0 | dry blend | not granulated with aspartame | | APM | 0.331 |
| | | | | | | B-cyclo. | 0.051 |
| 2 | Antifoam[b] | 2.0 | dry blend | not granulated with aspartame | | APM | 0.331 |
| | | | | | | Antifoam | 0.051 |
| 3 | B-cyclodextrin[a] | 4.0 | triturate/APM | not granulated with aspartame | | APM | 0.331 |
| | Antifoam[b] | 2.0 | dry blend | | | B-cyclo. | 0.102 |
| | | | | | | Antifoam | 0.051 |
| 4 | PVP/VA S-360[c] | 1.0 | dry blend | not granulated with aspartame | | APM | 0.331 |
| | | | | | | PVP/VA | 0.025 |
| 5 | PVP K-32[d] | 1.0 | dry blend | not granulated with aspartame | | APM | 0.331 |
| | PVP/VA S-630[c] | 1.0 | dry blend | | | PVP | 0.025 |
| | | | | | | PVP/VA | 0.025 |
| 6 | Simethicone[e] | 0.5 | 1% triturate in citric acid | not granulated with aspartame | | APM | 0.333 |
| | | | | | | Simeth. | 0.005 |
| 7 | Methocel E-15Prem[f] | 1.0 | dry blend | not granulated with aspartame | | APM | 0.333 |
| | | | | | | Methocel | 0.026 |
| 8 | Simethicone[e] | 0.2 | triturate/APM Simethicone Citric Acid | APM Simeth. Citric A. | 13.0 0.3 86.7 | APM Simeth. | 0.333 0.005 |
| 9 | Antifoam[g] | 0.3 | trit & mill APM/ Antifoam/Citric | APM Antifoam | 13.0 0.3 | APM Antifoam | 0.333 0.008 |

TABLE IV-continued

| Tablet Formula | Modifier (to control film formation) | Quantity (mg) | Method of Addition | % concentration in aspartame (APM) granule (where appropriate) | | % concentration in final tablet formula | |
|---|---|---|---|---|---|---|---|
| | | | Acid | Citric A. | 86.7 | | |
| 10 | Pluronic L-72[h] (Poloxamer 212) | 2.0 | G-2 Wet Granulation APM/Pluronic L-72/ Lactose | APM Plur. L72 Lactose | 6.8 1.1 92.1 | APM Plur. L72 | 0.331 0.051 |
| 11 | Pluronic F-38[h] (Poloxamer 108) | 2.0 | G-3 Wet Granulation APM/Pluronic F-38/ Lactose | APM Plur. F38 Lactose | 6.8 1.1 92.1 | APM Plur. F38 | 0.331 0.051 |
| 12 | Pluronic F-127[h] (Poloxamer 417) | 2.0 | G-4 Wet Granulation APM/Pluronic F-127 Lactose | APM Plur F127 Lactose | 6.8 1.1 92.1 | APM Plur F127 | 0.331 0.051 |
| 13 | Pluronic L-72[h] (Poloxamer 212) | 1.0 | G-5 Wet Granulation APM/Pluronic L-72/ Lactose | APM Plur. L72 Lactose | 6.9 0.5 92.6 | APM Plur. L72 | 0.333 0.026 |
| 14 | Pluronic L-72[h] (Poloxamer 212) | 0.6 | G-6 Wet Granulation APM/Pluronic L-72/ Lactose | APM Plur. L72 Lactose | 11.44 0.53 88.03 | APM Plur. L72 | 0.333 0.015 |
| 15 | Pluronic L-72[h] (Poloxamer 212) | 0.6 | G-8 Wet Granulation APM/Pluronic L-72/ Lactose | APM Plur. L72 Lactose | 11.44 0.53 88.03 | APM Plur. L72 | 0.333 0.015 |
| 16 | NONE - CONTROL | — | — | — | | — | |
| 17 | NONE - Sodium Bicarbonate replaces Calcium Carbonate | | | | | | |
| 18 | (8) Pluronic L-62[h] (Poloxamer 182) | 1.0 | G11 Wet Granulation APM/Pluronic L-62/ Lactose | APM Plur. L62 Lactose | 6.9 0.5 92.6 | APM Plur. L62 | 0.333 0.026 |
| 19 | (8) Pluronic L-92[h] (Poloxamer 282) | 1.0 | G12 Wet Granulation APM/Pluronic L-92/ Lactose | APM Plur. L92 Lactose | 6.9 0.5 92.6 | APM Plur. L92 | 0.333 0.026 |
| 20 | NONE - Calcium Saccharin replaces Aspartame | | | | | — | |

[a] Beta-Cyclodextrin MW 1135 Pfanstiehl Laboratories (Waukegan, Illinois 60085)
[b] Antifoam HC-401 Hodag Chemical Corporation (Skokie, Illinois 60076)
[c] PVP/VA S-362 (Polyvinylpyrrilidone vinyl acetate) GAF Corporation (New York, New York 10020)
[d] PVP (Polyvinylpyrrilidone - Plasdone K 29/32) GAF Corporation (New York, New York 10020)
[e] Medical Antifoam A Dow Corning Corporation (Midland, Michigan 48640)
[f] Methocel E-15 Premium Dow Chemical Company (Midland, Michigan 48674)
[g] Antifoam 70454 Rhone-Poulenc Inc. (Monmouth Junction, New Jersey 08852)
[h] Pluronic Polyols BASF Wyandotte Corporation, Parsippany (New Jersey 07054)

The observed results are summarized in Table V, below.

TABLE V

| Formulation | Maximum Foam Formation | Film Formation[a] |
|---|---|---|
| 1 | 70 ml | 165 ml |
| 2 | 90 ml | 265 ml |
| 3 | 65 ml | 290 ml |
| 4 | 115 ml | 215 ml |
| 5 | 150 ml | 0 |
| 6 | 40 ml | 190 ml |
| 7 | 40 ml | 360 ml |
| 8 | 20 ml | 290 ml |
| 9 | 65 ml | 365 ml |
| 10 | 110 ml | 0 |
| 11 | 160 ml | 0 |
| 12 | 300 ml | 0 |
| 13 | 65 ml | 0 |
| 14 | 55 ml | 0 |
| 15 | 55 ml | 0 |
| 16 | 80 ml | 265 ml |
| 17 | 90 ml | 0 |
| 18 | 35 ml | 0 |
| 19 | 60 ml | 0 |
| 20 | 20 ml | 0 |

[a] (Height of film in graduated cylinder above final liquid level measured by height in ml. graduated cylinder)

For formulation 18 a very thin light film of about 250 ml was observed. However it was sufficiently light to be of no substantial consequence, so the reported amount of undesirable film is zero.

The volume indicated under the heading "Maximum Foam Formation", in milliliters, is the approximate volume of the 500 milliliter graduated cylinder occupied by the foam, at the maximum point of foaming. The measurement under "Film Formation" is the height in the graduated cylinder, above the fluid level, to which the film extended. The number does not necessarily represent a specific volume of film, but rather a relative measure of its height in the graduated cylinder.

Generally, the only acceptable level of film formation is 0, or no observable film. In some instances, however, the film may be so light and thin that it is neither unsightly nor a problem with respect to formation and consumption of the overall aqueous calcium solution. An example of this is indicated by the results of formulation 18, wherein no troublesome film was formed even though a substantial amount of a very light film was observed. Foaming is unacceptable, or substantial, if much more than about 100 ml of foam are formed.

The above test results may be summarized as follows:

1. No surfactants other than those which are block copolymers of propylene oxide and ethylene oxide were observed to be effective in controlling film formation without excessive foaming.

2. The results of formulation 16 indicate that aspartame is indeed involved in film formation, since a control having no aspartame showed no film formation.

3. The results with formulation 17 suggest that calcium is also involved in the filming problem, since the replacement of calcium carbonate by sodium bicarbonate led to no film formation. This suggests utilization of the preferred surfactants, to control film formation, in almost any effervescent system containing calcium ions and aspartame together.

4. Formulation 10 probably approaches the upper limit in the amount of surfactant utilizable in association with the preferred levels of aspartame, according to the present invention. In formulation 10, a total of two milligrams of the surfactant poloxamer 212 was used in the formulation. This represents about 1.1 percent by weight of the aspartame granule or about 0.051 percent by weight of the overall tablet. The amount of aspartame present was about 6.8 percent by weight of the aspartame granule or about 0.331 percent by weight of the overall tablet. It can reasonably be concluded that this represents the higher practical level of surfactant for most uses, since at this level foaming approaches the extreme that is acceptable.

As suggested previously, the above-related results suggest a general method for control of film formation, when aspartame is used in solubilized calcium solutions. Film formation, without excessive foaming, can be obtained through the utilization of surfactants selected from a group of propylene oxide/ethylene oxide co-polymers that includes the three specific co-polymers listed above. Generally, however, it will be anticipated that a plurality of copolymers or mixtures of copolymers possessing the same, or similar, characteristics may be used.

As required, detailed embodiments of the present invention have been disclosed herein. However, it is to be understood that the disclosed embodiments are merely exemplary of the invention, which may be embodied in various forms. Therefore, specific details disclosed herein are not to be interpreted as limiting, but rather as a basis for the claims and as-a representative basis for teaching one skilled in the art to variously employ the present invention in virtually any appropriate system.

What is claimed is:

1. A method of inhibiting filming during formation of an aqueous solution containing effective amounts of soluble calcium and aspartame to provide a sweetened dietary supplement said method comprising providing in said solution an effective amount of a nonionic surfactant comprising a block copolymer of propylene oxide and ethylene oxide to inhibit substantial filming, the block copolymer having an average molecular weight of about 2,000–4,000.

2. A method of inhibiting filming during formation of an aqueous solution containing effective amounts of soluble calcium and aspartame to provide a sweetened dietary supplement; said method comprising providing in said solution an effective amount of a nonionic surfactant comprising a block copolymer of propylene oxide and ethylene oxide to inhibit substantial filming wherein:
   (i) said block copolymer has an average molecular weight of about 2,000–4,000;
   (ii) said block copolymer includes a poly(oxypropylene) hydrophobic base having an average molecular weight of 1,700–3,000; and,
   (iii) said block copolymer includes a hydrophilic poly(oxyethylene) component which is about 15–35% of the average molecular weight of said polymer.

3. The method according to claim 2 wherein said nonionic surfactant comprises CTFA Poloxamer 182, CTFA Poloxamer 212, CTFA Poloxamer 282 or mixtures thereof.

4. The method according to claim 3 wherein the weight ratio of the nonionic surfactant to the aspartame is about 1:2.5–350.

5. The method according to claim 3 wherein the weight ratio of the nonionic surfactant to the aspartame is about 1:18–25.

6. The method according to claim 2 wherein the weight ratio of the nonionic surfactant to the aspartame is about 1:2.5–350.

7. The method according to claim 2 wherein the weight ratio of the nonionic surfactant to the aspartame is about 1:18–25.

8. An improved effervescent tablet including calcium carbonate, an organic acid and aspartame, the improvement comprising inclusion in said tablet of an effective amount of a nonionic surfactant to inhibit substantial filming; the nonionic surfactant comprising a block copolymer of propylene oxide and ethylene oxide having an average molecular weight of about 2,000–4,000.

9. An improved effervescent tablet including effective amounts of calcium carbonate, an organic acid, and aspartame to provide a sweetened dietary supplement, the improvement comprising: inclusion in said tablet of a nonionic surfactant comprising a block copolymer of propylene oxide and ethylene oxide wherein:
   (i) said block copolymer has an average molecular weight of about 2,000–4,000;
   (ii) said block copolymer includes a poly(oxypropylene) hydrophobic base having an average molecular weight of 1,700–3,000; and,
   (iii) said block copolymer includes a hydrophilic poly(oxyethylene) component which is about 15–35% of the average molecular weight of said copolymer; wherein the amount of said nonionic surfactant is effective to prevent substantial film formation and foaming during the solubilization of the calcium carbonate and the aspartame.

10. The improved effervescent tablet according to claim 9 wherein the nonionic surfactant comprises CTFA Poloxamer 182, CTFA Poloxamer 212, CTFA Poloxamer 282 or mixtures thereof.

11. The improved effervescent tablet according to claim 9 wherein the weight ratio of the nonionic surfactant to the aspartame is about 1:2.5–350.

12. The improved effervescent tablet according to claim 9 wherein the weight ratio of the nonionic surfactant to the aspartame is about 1:18–25.

13. An effervescent tablet for providing an aspartame-sweetened, calcium ion-containing solution upon dissolution in aqueous media; said tablet compri(a)
   (a) about 10–90% calcium carbonate;
   (b) about 10–90% of an organic acid component wherein the organic acid component includes at least about 80% citric acid;
   (c) about 2–20% of a compression-enhancing vehicle;
   (d) about 0.03–3.3% aspartame, and
   (e) a nonionic surfactant including a block copolymer of propylene oxide and ethylene oxide; the block copolymer having an average molecular weight of about 2,000–4,000; wherein the amount of said nonionic surfactant is effective to prevent substantial film formation and foaming during solubilization of the calcium carbonate and the aspartame.

14. An effervescent tablet for providing an aspartame-sweetened, calcium ion-containing solution upon dissolution in aqueous media; said tablet compri(a)
   (a) about 10–90% calcium carbonate;
   (b) about 10–90% of an organic acid component wherein the organic acid component includes at least about 80% citric acid;
   (c) about 2–20% of a compression-enhancing vehicle;
   (d) about 0.03–3.3% aspartame, and
   (e) a nonionic surfactant including a block copolymer of propylene oxide and ethylene oxide wherein:

(i) said block copolymer has an average molecular weight of about 2,000–4,000;

(ii) said block copolymer includes a poly(oxypropylene) hydrophobic base having an average molecular weight of 1,700–3,000;

(iii) said block copolymer includes a hydrophilic poly(oxyethylene) component which is about 15–35% of the average molecular weight, of said copolymer; and, (iv) the amount of said nonionic surfactant is effective to prevent substantial film formation and foaming during solubilization of the calcium carbonate and the aspartame.

15. A tablet according to claim 14 wherein the nonionic surfactant comprises CTFA Poloxamer 182, CTFA Poloxamer 212, CTFA Poloxamer 282 or mixtures thereof.

16. The effervescent tablet according to claim 14 wherein the weight ratio of the nonionic surfactant to the aspartame is about 1:2.5–350.

17. The effervescent tablet according to claim 14 wherein the weight ratio of the nonionic surfactant to the aspartame is about 1:18–25.

18. A tablet according to claim 14 including:
(a) about 0.1–0.5% by weight aspartame; and,
(b) about 0.01–0.03% by weight of the block copolymer.

19. A tablet according to claim 18 wherein the nonionic surfactant comprises CTFA Poloxamer 182, CTFA Poloxamer 212, CTFA Poloxamer 282 or mixtures thereof.

20. A tablet for producing a solution containing calcium ions and aspartame; said tablet comprising:
(a) about 30–45% calcium carbonate granules; said calcium carbonate granules including about 75–90% CaCO$_3$ and about 5–25% compression-enhancing vehicle;
(b) about 40–55% citric acid;
(c) about 1–10% sorbitol;
(d) about 1–5% fumaric acid;
(e) about 0.05–0.25% glutamic acid;
(f) about 1–5% aspartame granules including:
  (i) about 5–15% aspartame; and
  (ii) about 0.1–1.5% nonionic surfactant comprising a block copolymer of propylene oxide and ethylene oxide wherein the block copolymer has an average molecular weight of about 2,000–4,000.

21. A tablet for producing a solution containing calcium ions and aspartame; said tablet comprising:
(a) about 30–45%,calcium carbonate granules; said calcium carbonate granules including about 75–90% CaCO$_3$ and about 5–25% compression-enhancing vehicle;
(b) about 40–55% citric acid;
(c) about 1–10% sorbitol;
(d) about 1–5% fumaric acid;
(e) about 0.05–0.25% glutamic acid; and
(f) about 1–5% aspartame granules including:
  (i) about 5–15% aspartame; and
  (ii) about 0.1–1.5% nonionic surfactant comprising a block copolymer of propylene oxide and ethylene oxide wherein the block copolymer has an average molecular weight of about 2,000–4,000, the copolymer includes a poly(oxypropylene) unit having an average molecular weight of 1,700–3,000, and the copolymer includes a hydrophilic poly(oxyethylene) compound which is about 15–35% of the average molecular weight of the copolymer.

22. The tablet according to claim 21 wherein the tablet has a mass of about 3,000–5,000 mg and includes:
(a) about 1,200–1,800 mg calcium carbonate granules;
(b) about 1,000–2,800 mg citric acid;
(c) about 100–200 mg fumaric acid; and
(d) about 50–150 mg aspartame granules 23. The tablet according to claim 22 including about 20–300 mg of compression-enhancing vehicle in addition to that contained in the calcium carbonate granules and the aspartame granules.

24. The tablet according to claim 22 wherein the block copolymer comprises CTFA Poloxamer 182, CTFA poloxamer 212, CTFA Poloxamer 282 or mixtures thereof 25. An aspartame granule composition for use in sweetening a calcium ion-containing aqueous solution; the aspartame granule composition comprising:
(a) an amount of aspartame effective to sweeten said calcium ion-containing solution; and
(b) an effective amount of nonionic surfactant comprising a block copolymer of propylene oxide and ethylene oxide wherein the block copolymer has an average molecular weight of 2,000–4,000.

26. The aspartame granule composition according to claim 25 wherein the block copolymer includes a poly(oxypropylene) hydrophobic base having an average molecular weight of about 1,700–3,000 and the block copolymer includes a hydrophilic poly(oxypropylene) component which is about 15–35% of the molecular weight of the copolymer.

27. The composition according to claim 26 wherein the block copolymer comprises CTFA Poloxamer 182, CTFA poloxamer 212, CTFA Poloxamer 282 or mixtures thereof.

28. The composition according to claim 26 wherein the weight ratio of the nonionic surfactant to the aspartame is about 1:18–25.

29. An aspartae granule composition for use in sweetening a calcium ion-containing aqueous solution; the aspartame granule composition comprising:
(a) about 5–35% aspartame;
(b) about 65–95% compression-enhancing vehicle; and
(c) about 0.1–2% nonionic surfactant comprising a block copolymer of propylene oxide and ethylene oxide having an average molecular weight of about 2,000–4,000.

30. The aspartame granule composition of claim 29 wherein the block copolymer composes: a poly(oxypropylene) unit having an average molecular weight of 1,700–3,000; and, a hydrophilic poly(oxyethylene) component which is about 15–35% of the average molecular weight of the copolymer.

31. An aspartame granule composition according to claim 30 wherein the copolymer comprises CTFA Poloxamer 182, CTFA Poloxamer 212, CTFA Poloxamer 282 or mixtures thereof.

32. A method of preparing aspartame granules for use in sweetening solutions containing calcium ions; said method comprising the steps of:
(a) preparing a dry blend of aspartame and a compression-enhancing vehicle; the dry blend including about 5–35% aspartame and about 65–95% compression enhancing vehicle;
(b) mixing the dry blend from step (a) in a suitable granulator with an aqueous solution comprising about 2.5–10.0% of a nonionic surfactant so as to disperse said surfactant throughout said dry blend; wherein said surfactant includes a block copolymer of propylene oxide and ethylene oxide wherein the block copolymer has an average molecular weight of about 2,000–4,000, and (c) drying the aspartame granules.

33. The method according to claim 32 wherein the block copolymer includes a poly(oxypropylene) hydrophobic base having an average molecular weight of about 1700–3000 and the block copolymer includes a hydrophilic poly(oxypropylene) having a molecular weight which is about 15–35% of the average molecular weight of the copolymer.

34. The method of claim 32 wherein said dried aspartame granules comprise about 0.25–2.5% by weight surfactant.

35. The method according to claim 32 wherein step (c) includes heating said aspartame granules to about 120°–130° F.

* * * * *